United States Patent
Bhuyan et al.

(10) Patent No.: US 9,573,865 B2
(45) Date of Patent: Feb. 21, 2017

(54) PROCESS FOR PRODUCTION OF C3 OLEFIN IN A FLUID CATALYTIC CRACKING UNIT

(71) Applicant: INDIAN OIL CORPORATION LTD., Kolkata, West Bengal (IN)

(72) Inventors: Manoj Kumar Bhuyan, Faridabad (IN); Debasis Bhattacharyya, Faridabad (IN); Gopinath Bhanuprasad Sayapaneni, Faridabad (IN); Somnath Kukade, Faridabad (IN); Satheesh Kumaran Vetterkunnel, Faridabad (IN)

(73) Assignee: INDIAN OIL CORPORATION LTD., Kolkata (IN)

( * ) Notice: Subject to any disclaimer, the term of this patent is extended or adjusted under 35 U.S.C. 154(b) by 281 days.

(21) Appl. No.: 14/347,797

(22) PCT Filed: Oct. 11, 2012

(86) PCT No.: PCT/IB2012/002027
§ 371 (c)(1),
(2) Date: Mar. 27, 2014

(87) PCT Pub. No.: WO2013/054173
PCT Pub. Date: Apr. 18, 2013

(65) Prior Publication Data
US 2014/0257006 A1    Sep. 11, 2014

(30) Foreign Application Priority Data
Oct. 12, 2011 (IN) ............................ 1314/KOL/2011

(51) Int. Cl.
*C07C 4/06* (2006.01)
*C10G 11/18* (2006.01)

(52) U.S. Cl.
CPC ................ *C07C 4/06* (2013.01); *C10G 11/18* (2013.01); *C10G 11/187* (2013.01);
(Continued)

(58) Field of Classification Search
None
See application file for complete search history.

(56) References Cited

U.S. PATENT DOCUMENTS 4,789,458 A * 12/1988 Haddad .................. C10G 11/18
                                                  208/113
4,840,928 A    6/1989 Harandi et al.
(Continued)

FOREIGN PATENT DOCUMENTS

EP    0 325 437 A2    7/1989

*Primary Examiner* — In Suk Bullock
*Assistant Examiner* — Alyssa L Cepluch
(74) *Attorney, Agent, or Firm* — Maschoff Brennan

(57) ABSTRACT

A process for increasing the yield of $C_3$ olefin in fluidized bed catalytic cracking of hydrocarbon feedstocks is disclosed. $C_4$ fraction produced from the cracking of hydrocarbon feedstock in the primary reaction zone (riser), optionally with external source of $C_4$ stream is fed into the stripper which acts as a secondary reaction zone at an elevated temperature and at an optimum WHSV. The elevated temperature is achieved by injecting a part of the regenerated catalyst from regenerator, which is at a higher temperature, directly into the stripper through a dedicated additional lift line. This raises the activity of catalyst inside the stripper. The direct injection of regenerated catalyst into the stripper, besides producing higher yields of propylene, improves the stripping efficiency leading to enhanced recovery of strippable hydrocarbons.

6 Claims, 1 Drawing Sheet

(52) U.S. Cl.
CPC ............ *C10G 2300/107* (2013.01); *C10G 2300/1044* (2013.01); *C10G 2300/1077* (2013.01); *C10G 2300/4006* (2013.01); *C10G 2300/4025* (2013.01); *C10G 2300/4081* (2013.01); *C10G 2300/4093* (2013.01); *C10G 2300/708* (2013.01); *C10G 2400/20* (2013.01)

(56) References Cited

U.S. PATENT DOCUMENTS

| | | | |
|---|---|---|---|
| 5,043,517 A * | 8/1991 | Haddad | B01J 29/90 502/42 |
| 5,348,642 A | 9/1994 | Serrand et al. | |
| 5,597,537 A | 1/1997 | Wegerer et al. | |
| 7,374,660 B2 | 5/2008 | Steffens et al. | |
| 2003/0006168 A1* | 1/2003 | Ino | C10G 11/18 208/120.01 |
| 2004/0060846 A1 | 4/2004 | Letzsch | |
| 2008/0093263 A1 | 4/2008 | Cheng | |

* cited by examiner

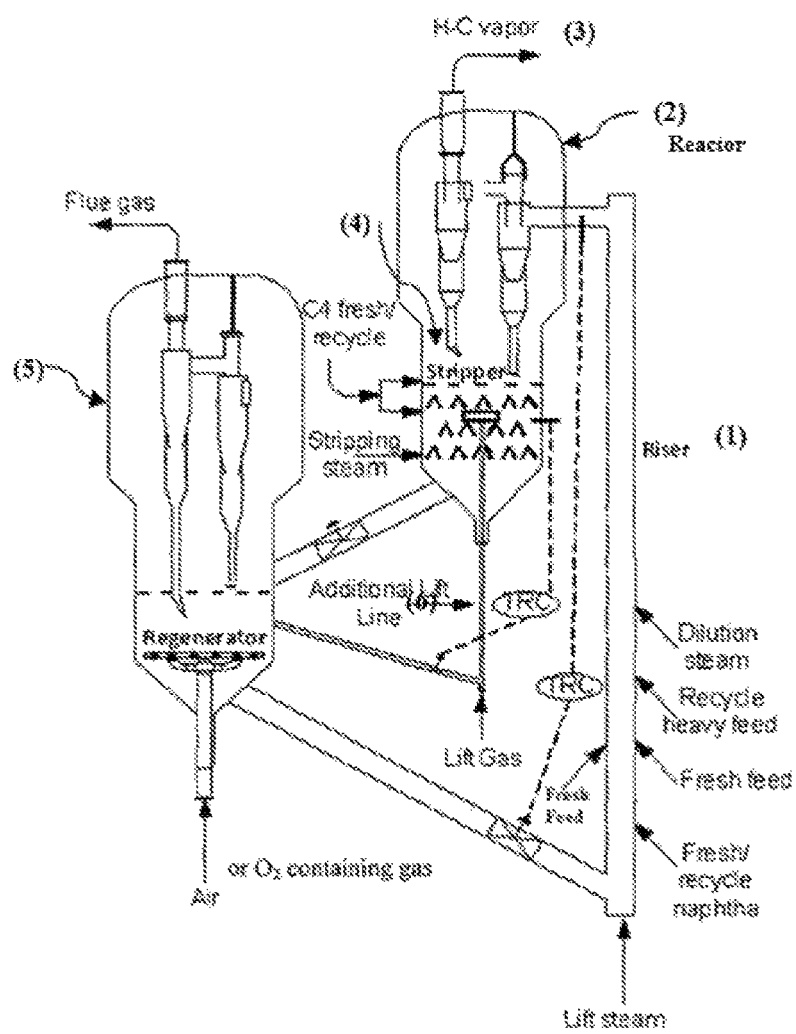

PROCESS FOR PRODUCTION OF C3 OLEFIN IN A FLUID CATALYTIC CRACKING UNIT

FIELD OF THE INVENTION

The present invention relates to the conversion of hydrocarbon feedstock in Fluid Catalytic Cracking (FCC) unit in general, and to a process for production of $C_3$ olefin in a fluid catalytic cracking unit in particular. The invention discloses a process for selective conversion of $C_4$ hydrocarbons to higher yield of propylene in a FCC unit.

BACKGROUND OF THE INVENTION AND ITS PRIOR ART

Fluid Catalytic Cracking (FCC) is the most important conversion process used in petroleum refineries. It is widely used to convert the high-boiling, high-molecular weight hydrocarbon fractions of petroleum crude oils to more valuable gasoline, olefinic gases, and other products. Cracking of petroleum hydrocarbons was originally done by thermal cracking, which has been almost completely replaced by catalytic cracking because of its adaptability towards improved and selective cracking to produce high octane gasoline and valuable lighter olefinic gaseous products. This process also provides flexibility to be tuned to different modes of operational window in order to maximize the product of interest.

The conversion section of FCC unit consists of riser, reactor, stripper, regenerator and their associated hardware internals. The feed is injected into the up-flowing catalyst at the bottom of the riser. Steam is introduced along with the feed for proper atomization. The feed molecules are cracked inside the riser when they are contacted with hot regenerated catalyst producing product vapors and coke. The catalyst activity is reduced due to deposition of coke on the catalyst. The cracked products along with the catalyst move up through the riser and the primary disengagement of the catalyst from the hydrocarbon vapor is achieved through riser termination device. The hydrocarbon vapor after separation from catalyst is fed to a fractionation section for separation into various cuts. The separated spent catalyst is steam stripped in stripper to recover trapped hydrocarbons inside the catalyst pores. The stripped spent catalyst flows to regenerator wherein the coke deposited on the spent catalyst is burnt off in presence of air and/or oxygen containing gases to restore the catalyst activity. The hot regenerated catalyst is subsequently recycled back to the riser bottom to complete the cycle.

The demand for light olefins like ethylene and propylene as building blocks for the production of petrochemicals will continue to grow. Propylene demand growth rate outpaces ethylene due to high demand of poly-propylene and other propylene derivatives. The conventional steam cracking units, which are more energy intensive, cannot meet the incremental demand of propylene as its propylene to ethylene ratio is low. Furthermore, much of the new steam cracking capacity is based on ethane feed, which produces little propylene. Therefore, although steam cracking continues to supply most of the world's propylene, there is an increasing need for production of propylene from other sources.

The present invention discloses a process to substantially increase the propylene yield through selective conversion of $C_4$ hydrocarbons in a FCC unit.

U.S. Pat. No. 5,348,642 discloses a catalytic cracking process and apparatus wherein a part of hot regenerated catalyst is passed directly from the regenerator to the stripping zone via a conduit to increase the stripping zone temperature resulting in improved recovery of hydrocarbons from the spent catalyst.

The conversion of the feed-stocks processed is optimized as per the product slate requirement by designing the reaction of severity, i.e. reactor outlet temperature (ROT) and catalyst to oil ratio (C/O). In a FCC unit, ROT is the measured variable which is achieved by controlling catalyst circulation rate (CCR) to the riser bottom from the regenerator vessel. At constant feed rate, increase in ROT leads to a higher CCR and thus a higher CO inside the riser. There are prior art inventions where the C/O has been increased without changing ROT.

U.S. Pat. No. 5,597,537 discloses an FCC apparatus which mixes a part of spent catalyst with regenerated catalyst in a separate chamber to obtain a blended catalyst stream before contacting with feed. Mixing of the spent catalyst (normally at lower temperature) with regenerated catalyst (normally at higher temperature) in the mixing chamber results in a lower equilibrium temperature at the riser bottom leading to increase in catalyst circulation rate (CCR) at a given reactor outlet temperature (ROT). However, this prior art doesn't teach cracking of $C_4$ hydrocarbons to $C_3$ olefins.

US Application US20040060846A1 discloses a deep catalytic cracking process to produce increased yields of $C_3$ and $C_4$ olefins at the expense of $C_2$ olefins. In this invention, the riser reactor is configured to have two different radii in order to produce improved selectivity to $C_3$ and $C_4$ olefins as products. In the second broader riser section, Weight Hourly Space Velocity (WHSV) is significantly lowered, so that gasoline range molecules produced in the first narrower section is cracked to produce high yields of the light olefins. However, the prior art does not teach any method that is directed specifically to conversion of $C_4$ hydrocarbons to $C_3$ olefins.

U.S. Pat. No. 7,374,660B2 discloses a process for selectively producing $C_3$ olefins from a cracked naphtha stream. A stream rich in $C_4$ olefins is recycled to a dilute phase reaction zone in the stripping zone separate from the dense phase of the stripping zone to improve the propylene selectivity. However, this prior art doesn't provide any means for achieving optimum temperature and catalyst activity which facilitates maximum propylene yield.

In the present invention, an optimum condition of WHSV, temperature as well as catalyst activity is achieved for enhanced production of propylene from cracking of $C_4$ fraction. A part of the regenerated catalyst is injected into the stripper bed for achieving the required temperature and catalyst activity.

The present invention results in augmentation of conversion of $C_4$ into $C_3$ olefins.

OBJECTS OF THE INVENTION

It is therefore an object of the invention to provide a process to substantially increase the propylene yield through selective conversion of $C_4$ hydrocarbons in a given FCC unit.

Another object of the invention is to provide a process, wherein the additional propylene production takes place inside the stripper, wherein a part of the regenerated catalyst is directly fed into the stripper to provide optimum temperature and catalyst activity without increasing the capacity of the riser.

Another object of the invention is to provide a process, wherein the additional propylene production doesn't require any change in process conditions inside the riser allowing its operation to achieve the desired product slate.

Yet another object of the invention is to provide a process, wherein the efficiency of the stripper improves due to the higher temperature caused by recycle of part of hot regenerated catalyst.

A still further object of the invention is to provide a process for converting product $C_4$ stream obtained from the cracking of feed in the riser with or without any external $C_4$ stream to high yield of propylene.

SUMMARY OF THE INVENTION

The present invention is a process for selective conversion of $C_4$ hydrocarbons to higher yield of propylene in a FCC unit. This is achieved by cracking $C_4$ hydrocarbons in a reaction zone of optimum WHSV (stripper bed) and at higher temperature achieved through injecting a part of regenerated catalyst directly into the reaction zone using an additional catalyst transfer line. This invention provides the optimum reaction severity in terms of both temperature and WHSV for enhancing the crackability of $C_4$ stream to produce propylene.

BRIEF DESCRIPTION OF THE ACCOMPANYING DRAWING

FIG. 1 shows the schematic diagram of Riser-Stripper-Regenerator section of FCC unit according to the invention, which has been provided with a dedicated catalyst lift line for direct transfer of a part of hot regenerated catalyst from regenerator to the stripper.

DESCRIPTION OF THE INVENTION

The invention will now be described in an exemplary and non-limiting embodiment as depicted in the accompanying drawing. There can, however, be other embodiments of the same invention, all of which are deemed covered by this description.

In the riser-stripper-regenerator section of the FCC unit shown in FIG. 1, feed is injected into the up-flowing catalyst at the bottom of the riser (1). Steam is introduced along with the feed for proper atomization. Vaporization and cracking of the feed takes place as it comes in contact with the hot regenerated catalyst and the whole mixture moves along the riser in upward direction. The hydrocarbon feed is cracked in the riser (1) in presence of fluidizable solid microspherical cracking catalyst to produce hydrocarbon products and coke.

The hydrocarbon products are then separated from the spent catalyst by proper disengagement system. The separated hydrocarbon vapor (3) is fed to fractionation section for separation into various products. The coke deposited spent catalyst is then stripped with steam in the stripper (4) to remove the hydrocarbons entrapped inside the catalyst pores. The stripped spent catalyst is fed to the regenerator (5), where the coke is burnt off in presence of air and/or oxygen containing gases to produce reactivated regenerated catalyst. Major part of the hot regenerated catalyst is circulated to riser bottom to complete the cycle.

In the present invention, for increasing the propylene yield, the $C_4$ hydrocarbon fraction separated from the cracked products, optionally with external source of $C_4$ hydrocarbon stream is cracked in the stripper bed of optimum WHSV.

The desired extent of cracking of $C_4$ stream does not take place in stripper due to lower temperature, catalyst activity and higher heat of reaction. For $C_4$ cracking, optimum catalyst activity as well as high temperature is necessary. In order to achieve these conditions, in the present invention, a part of hot regenerated catalyst is taken from the regenerator (5) and injected into the stripper bed (4) through an additional lift line (6) with the help of a lift media. So, the required conditions of higher temperature, optimum catalyst activity as well as optimum WHSV are met in a novel and innovative way in the stripper for achieving increased $C_3$ olefin production.

The catalyst identity that is entering into the stripper is changed by mixing a part of hot regenerated catalyst with spent catalyst, whereas there is no change in the catalyst identity in the riser.

In the present invention, $C_4$ stream is injected into the stripper (4) operated at WHSV in the range of 5 to 50 $hr^{-1}$ at an elevated temperature above 550° C.

The riser (1) is operated at ROT in the range of 500 to 625° C. with circulating catalyst comprising of more than 5 wt % pentasil zeolite based additive.

In the present invention, two TRC units are used in the apparatus (as shown in FIG. 1); one at the riser and other at the stripper. The "TRC" as referred in the context of the present invention means "Temperature Recorder and Controller". It is used for measuring temperature at the riser outlet and inside the stripper and controlling the flow of hot catalyst through a control valve in order to achieve the desired temperature at the riser outlet (measuring point) as well as inside the stripper )measuring point).

Lift media such as fuel gas, which comprises lighter hydrocarbons up to $C_2$, other light hydrocarbon streams, steam etc are used in the dedicated additional lift line (6). This line can easily be retro-fitted into any existing FCC unit.

Coke on the circulating catalyst in the stripper (4) is kept in the range of 0.3 to 1 wt %.

The direct injection of a part of hot regenerated catalyst into the stripper, besides producing higher yields of propylene, improves the stripping efficiency which leads to enhanced recovery of strippable hydrocarbons.

EXAMPLES

The examples given in this section are for illustration purpose only and don't construe to the claims as mentioned in subsequent, section. The data are based on microreactor and pilot plant tests as well as preliminary engineering calculation. The study was carried out with a residue feed having 4.4 wt % conradson carbon residue (CCR) and 941 kg/m³ density. The catalyst used in this study is a mixture of FCC catalyst having average particle size of 80 microns based on USY zeolite and an additive based on pentasil zeolite having silica to alumina molar ratio of 30. The catalyst was hydrothermally deactivated at 810° C. for 5 hrs. The reaction temperature for catalytic cracking of the residue feed was maintained at 580° C. for all cases. Cracking the residue feed in reactor riser without any $C_4$ cracking is considered as the 'Base case' for comparison purpose.

Cracking of $C_4$ stream both fresh and recycle is carried out in the stripper bed at optimum WHSV in the new cases.

Example-I

This example demonstrates the improvement in propylene yield in FCCU obtained through cracking of the product $C_4$ stream generated out of cracking of residue feed in the riser. The composition of $C_4$ stream used in the study is given in Table-I. The improvement in propylene yield on fresh feed basis with recycle of $C_4$ product into stripper without and with direct transfer of regenerated catalyst into stripper is presented in Table-II. Case I considers the recycle of $C_4$ stream without any transfer of hot regenerated catalyst into the stripper and therefore, reactions are conducted at a temperature close to riser outlet temperature. In Case-II, about 20 wt % of total catalyst flow from regenerator is directly transferred to the stripper which in turn increases the temperature to 600° C.

TABLE I

Composition of $C_4$ recycle stream

| Components | wt % |
| --- | --- |
| i-butane | 23.6 |
| n-butane | 6.5 |
| 1-butene | 15 |
| i-butylene | 26.4 |
| cis-2-butene | 11.7 |
| trans-2-butene | 16 |
| 1,3-butadiene | 0.8 |

TABLE II

| | | Base case | Case-I | Case-II |
| --- | --- | --- | --- | --- |
| Stripper zone temp | ° C. | 580 | 575 | 600 |
| Stripper zone WHSV | hr$^{-1}$ | — | 10 | 10 |
| $C_4$ recycle rate | wt % FF | — | 13 | 13 |
| Propylene Yield | wt % FF | 17.1 | 18.7 | 19.9 |
| Ethylene Yield | wt % FF | 4.3 | 5.1 | 5.7 |

In both Cases I and II, $C_4$ product corresponding to 13 wt % of fresh feed is recycled to the stripper and an improvement in propylene yield of 1.2 wt % on fresh feed basis is realized in Case-II over Case-I. Ethylene, one of the important petrochemical feed stocks, is predominantly produced employing steam cracking process. Using the process of the present invention, it is also possible to enhance the ethylene production and thereby make the economics more attractive. From Table-II, it is noted that an improvement in ethylene yield of 0.6 wt % on fresh feed basis is achieved in Case-II over Case-I. In this example, a residue feed has been used with which ex-riser $C_4$ quantity is coming to be 13 wt %. In the cases of using better quality feed, ex-riser $C_4$ quantity will increase which in turn will make the increase in propylene yield higher than 1.2 wt % as indicated above using the present invention.

Example-II

This example demonstrates the improvements in propylene yield in FCCU obtained through cracking of $C_4$ stream from an external source. The composition of $C_4$ stream used in the study is given in Table-III. Case-III and IV as given in Table-IV consider cracking of $C_4$ feed without and with direct transfer of regenerated catalyst into stripper respectively. In Case-IV, about 20 wt % of total catalyst flow from regenerator is directly transferred to the stripper to raise the temperature to 600° C. The quantity of $C_4$ stream was kept same as that of the earlier cases to maintain the same WHSV. Since the $C_4$ stream is external and it is included in the fresh feed quantity, the percentage of $C_4$ stream on fresh feed basis is coming lower than that of Example-I. Improvement in yields of propylene and ethylene in Case-IV over Case-III is 1.6 wt % and 0.7 wt % on fresh feed basis respectively.

TABLE III

Composition of external $C_4$ stream

| Components | wt % |
| --- | --- |
| i-butane | 34.7 |
| n-butane | 0.9 |
| 1-butene | 2.0 |
| i-butylene | 61.1 |
| cis-2-butene | 0.1 |
| trans-2-butene | 1.1 |
| 1,3-butadiene | 0.1 |

TABLE IV

| | | Base case | Case-III | Case-IV |
| --- | --- | --- | --- | --- |
| Stripper zone temp | ° C. | 580 | 575 | 600 |
| Stripper zone WHSV | hr$^{-1}$ | — | 10 | 10 |
| $C_4$ feed rate | wt % FF | — | 11.6 | 11.6 |
| Propylene Yield | wt % FF | 17.1 | 17.3 | 18.9 |
| Ethylene Yield | wt % FF | 4.3 | 4.9 | 5.6 |

We claim:

1. A process for enhancing the yield of propylene in a fluid catalytic cracking unit, the process comprising the steps of,
    a) cracking a hydrocarbon feed in a riser operated in a temperature range of 500° C. to 625° C. in presence of fluidized solid micro-spherical cracking catalyst to produce hydrocarbon products comprising propylene;
    b) separating coke laden spent catalyst from the hydrocarbon products and stripping it with steam in a stripper to remove the hydrocarbons entrapped inside the catalyst pores;
    c) burning off the coke deposited on the spent catalyst in a regenerator to obtain hot regenerated catalyst comprising coke in the amount of 0.3 to 1 wt %;
    d) recycling a part of the hot regenerated catalyst into the stripper to achieve a temperature inside the stripper in the range of 550 to 650° C. and recycling the remaining part of the hot regenerated catalyst to the riser bottom;
    e) injecting $C_4$ hydrocarbon fraction separated from the hydrocarbon products, optionally with external $C_4$ hydrocarbon stream, into the stripper to achieve WHSV in the range of 5 to 50 hr$^{-1}$.

2. The process as claimed in claim 1, wherein a part of the regenerated catalyst is passed to the stripper through a dedicated additional lift line using lift media comprising a fuel gas comprising lighter hydrocarbons up to $C_2$ and steam.

3. The process as claimed in claim 1, wherein the $C_4$ hydrocarbon fraction, optionally with external $C_4$ hydrocarbon stream is split injected at multiple elevations in the stripper depending on olefin content in the $C_4$ stream and axial temperature profile in the stripper.

4. The process as claimed in claim 1, wherein the cracking catalyst comprises more than 5 wt % pentasil zeolite based additive.

5. The process as claimed in claim 1, wherein the hot regenerated catalyst is directly injected into the stripper.

6. The process as claimed in claim 1, wherein the hydrocarbon feed processed in the riser comprises heavy vacuum gas oil, atmospheric tower bottom, coker heavy gas oil, once through hydrocracker bottom optionally with naphtha, individually or a combination thereof with or without vacuum tower bottom.

\* \* \* \* \*